US009844400B2

(12) United States Patent
Stevenson et al.

(10) Patent No.: US 9,844,400 B2
(45) Date of Patent: Dec. 19, 2017

(54) INSTRUMENT AND METHOD FOR PROVISIONALLY LOCKING A POLYAXIAL SCREW

(71) Applicant: Alphatec Spine, Inc., Carlsbad, CA (US)

(72) Inventors: Tara Stevenson, La Jolla, CA (US); Wally Gillespie, Carlsbad, CA (US); Clark Hutton, Carlsbad, CA (US)

( * ) Notice: Subject to any disclaimer, the term of this patent is extended or adjusted under 35 U.S.C. 154(b) by 137 days.

(21) Appl. No.: 14/058,144

(22) Filed: Oct. 18, 2013

(65) Prior Publication Data
US 2014/0180298 A1    Jun. 26, 2014

Related U.S. Application Data

(60) Provisional application No. 61/716,458, filed on Oct. 19, 2012.

(51) Int. Cl.
*A61B 17/70* (2006.01)
(52) U.S. Cl.
CPC ........ *A61B 17/7082* (2013.01); *A61B 17/708* (2013.01)

(58) Field of Classification Search
CPC .................................. A61B 17/7074–17/7091
See application file for complete search history.

(56) References Cited

U.S. PATENT DOCUMENTS

| 7,481,813 | B1 * | 1/2009 | Purcell ............... | A61B 17/7091 606/86 A |
| 2009/0228054 | A1 * | 9/2009 | Hoffman et al. ........... | 606/86 A |
| 2012/0089150 | A1 * | 4/2012 | Smith ........................... | 606/104 |

* cited by examiner

*Primary Examiner* — David Bates
*Assistant Examiner* — Olivia C Chang
(74) *Attorney, Agent, or Firm* — Dinsmore & Shohl LLP (57) ABSTRACT

An instrument for provisionally tightening a screw body member to a head of a polyaxial bone screw includes a barrel body, an inner shaft, a handle and lever, and a load link assembly. The barrel body includes a distal end with a pair of rotatable tangs configured to engage the screw body member. The inner shaft includes a distal end configured to engage a bushing within the screw body member. The lever pivotally couples to one of the handle and the barrel body. The load link assembly couples to the inner shaft and the lever. Actuation of the lever towards causes the load link assembly to longitudinally displace the inner shaft toward the distal end to contact the bushing and advance the bushing into frictional fit between the screw body member and the head of the polyaxial bone screw.

14 Claims, 7 Drawing Sheets

INSTRUMENT AND METHOD FOR PROVISIONALLY LOCKING A POLYAXIAL SCREW

CROSS-REFERENCE TO RELATED APPLICATIONS

The present application claims priority to U.S. Provisional Application Ser. No. 61/716,458 entitled "Instrument and Method for Provisionally Locking a Polyaxial Screw" which was filed on Oct. 19, 2012 and is incorporated herein by reference in its entirety.

FIELD

The present invention relates generally to systems for fixation of screws in the spine or bone, and more particularly to an instrument for provisionally tightening a screw body of the screw.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature.

Generally the correct curvature is obtained by manipulating the vertebrae into their proper position and securing that position with a rigid system of screws, rods, intervertebral spaces, and/or plates. The various components of the system may be surgically inserted through open or minimally invasive surgeries. The components may also be inserted through various approaches to the spine including anterior, lateral, and posterior approaches and others in between.

Spinal fixation systems may be used in surgery to align, adjust, and/or fix portions of the spinal column, i.e., vertebrae, in a desired spatial relationship relative to each other. Many spinal fixation systems employ a spinal rod for supporting the spine and for properly positioning components of the spine for various treatment purposes. Vertebral anchors, comprising pins, bolts, screws, and hooks, engage the vertebrae and connect the supporting rod to different vertebrae. The size, length, and shape of the cylindrical rod depend on the size, number, and position of the vertebrae to be held in a desired spatial relationship relative to each other by the apparatus.

During spinal surgery, a surgeon first exposes the spine posterior and attaches the vertebral anchors to selected vertebrae of the spine. The surgeon then inserts a properly shaped spinal rod into rod-receiving portions of the vertebral anchors to connect the selected vertebrae, thereby fixing the relative positions of the vertebrae. Generally, a controlled mechanical force is required to bring together the spinal rod and a spinal implant, such as the vertebral anchors, in a convenient manner. After insertion, a surgeon must insert a locking mechanism, such as a set screw, into the vertebral anchor to lock the spinal rod to the implant after the force for inserting the rod is removed.

Patients suffering from orthopedic injuries, deformities, or degenerative diseases often require surgery to stabilize an internal structure, promote healing, and/or relieve pain. In the spinal field, surgeries to correct spinal abnormalities often involve positioning one or more elongate stabilization elements such as rods, plates or other types of elongate members along a portion of the spinal column, and anchoring each of the elongate stabilization elements to two or more vertebrae via screws, hooks or other types of bone anchors. Prior to anchoring the elongate stabilization element to the spinal column, the surgeon may need to measure the distance between the bone anchors or between two reference locations along the spinal column in order to determine the appropriate length of the elongate stabilization element. In some instances, the bone anchors may be arranged at varying angular orientations, thereby presenting difficulties in accurately measuring the distance between the bone anchors to provide a properly sized elongate stabilization element having a length sufficient for coupling to the bone anchors.

Certain spinal conditions, including a fracture of a vertebra and a herniated disc, indicate treatment by spinal immobilization. Several systems of spinal joint immobilization are known, including surgical fusion and the attachment of pins and bone plates to the affected vertebrae. Known systems include screws having proximal heads and threaded shafts that may be inserted into at least two spaced-apart vertebras. Each screw includes a receiver attached over the head such that a stabilization rod can interconnect two or more receivers to immobilize the vertebras spanned by the screws.

Spinal immobilization systems typically require the threaded securement of some form of bone anchor and the like or bone screw-assembly into two or more vertebrae, which entails the drawing of the rod to the anchors/screw-assemblies, or drawing the anchors/screw-assemblies to the rod. Spinal screw-assemblies are used to secure a stabilization rod and comprise various components including a pedicle screw and a body member. The design of the spinal screw-assemblies allows for variable angular movement of the body member with respect to the pedicle screw with a threaded shaft portion of the screw extending through an opening in an end of the body member. However, in these systems, in order to tighten the spinal screw-assembly at a specific angle, a rod and a set screw must first be inserted, the components are tightened, and then the rod and set screw are removed.

The present invention helps to expedite the time of surgery by allowing a medical professional to provisionally tighten the spinal screw-assembly at a specific angle prior to placing a rod or set screw into the body member.

SUMMARY

Provided herein are apparatuses, systems, and methods of use for a screw head locker. The instrument for provisionally tightening or locking a screw body member to a head of a polyaxial bone screw, generally comprises: a barrel body having a proximal end and a distal end, the distal end having at least one tang for releasably engaging a screw body pocket on the screw body member; an inner shaft coaxially disposed between the tang, wherein the inner shaft includes distal engagement portion; and a lever operably coupled to the inner shaft, wherein the lever distally displaces the inner shaft to engage with a bushing member to lock the polyaxial motion of a screw displaced beneath the bushing member.

An instrument for tightening a screw body member to a head of a polyaxial bone screw includes a barrel body, an inner shaft, and a lever. The barrel body includes a proximal end and a distal end, the distal end having at least one tang for releasably engaging a screw body pocket on the screw body member. The inner shaft is coaxially disposed between the tangs and includes distal engagement portion. The lever is operably coupled to the inner shaft. The lever distally displaces the inner shaft to engage with a bushing member to lock the polyaxial motion of a screw displaced beneath the bushing member.

In other features, the lever is operably coupled to a load link assembly to distally displace the inner shaft into the screw body member to contact the bushing. The load link assembly includes first and second portions pivotally coupled together and coupled to the lever by a transfer link.

An instrument for provisionally tightening a screw body member to a head of a polyaxial bone screw includes a barrel body, an inner shaft, a load link assembly, and a lever. The barrel body includes a proximal end and a distal end, the distal end having a pair of tangs for releasably engaging a pair of screw body pockets on the screw body member. The inner shaft is disposed within the barrel body. The load link assembly operably couples to the inner shaft to the body. The lever extends from the load link assembly, the lever being movable to actuate the load link assembly. Actuation of the load link assembly displaces the inner shaft to engage a bushing disposed between the screw body member and the head of the polyaxial bone screw.

In other features, the inner shaft is longitudinally disposed between the tangs. Displacement of the lever after load link assembly actuation longitudinally displaces the inner shaft proximally from the bushing. The tangs releasably engage with the screw body pockets.

An instrument for provisionally tightening a screw body member to a head of a polyaxial bone screw includes a barrel body, an inner shaft, a handle and lever, and a load link assembly. The barrel body includes a distal end with a pair of rotatable tangs configured to engage the screw body member. The inner shaft includes a distal end configured to engage a bushing within the screw body member. The lever pivotally couples to one of the handle and the barrel body. The load link assembly couples to the inner shaft and the lever. Actuation of the lever towards causes the load link assembly to longitudinally displace the inner shaft toward the distal end to contact the bushing and advance the bushing into frictional fit between the screw body member and the head of the polyaxial bone screw.

In other features, the pair of tangs releasably engages a pair of screw body pockets. The inner shaft is coaxially disposed between the tangs. A lever extends from the load link assembly, wherein the lever is movable to actuate the load link assembly. Displacement of the lever after load link assembly actuation longitudinally displaces the inner shaft towards the proximal end of the barrel body. A bias spring biases the lever away from the handle to return the load link assembly to a rest position, wherein the inner shaft advances away from the distal end. The load link assembly comprises first and second portions pivotally coupled together such that actuation of the handle causes the at least one of the portions to advance towards a proximal end of the inner shaft. The pair of tangs are biased towards engagement with the screw body member by a pair of bias members within the distal end of the barrel body.

The apparatuses, systems, and methods of use are set forth in part in the description which follows, and part will be obvious from the description or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

DETAILED DESCRIPTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The words proximal and distal are applied to denote specific ends of components of the current invention described herein. A proximal end refers to the end of a component nearer to a medical professional when operating the component. A distal end refers to the end of the component further from the medical professional when operating the component.

The present invention helps to expedite the time of surgery by allowing a medical professional to provisionally tighten or lock the spinal screw-assembly at a specific angle prior to placing a rod or set screw into the body member.

Figure 1:
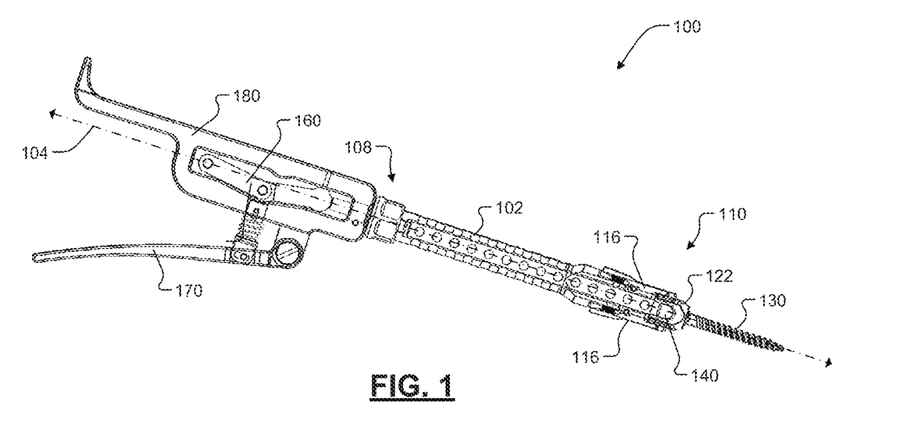
FIG. 1 is a perspective view of an instrument for tightening a screw body according to the principles of the present disclosure.
Figure 2:
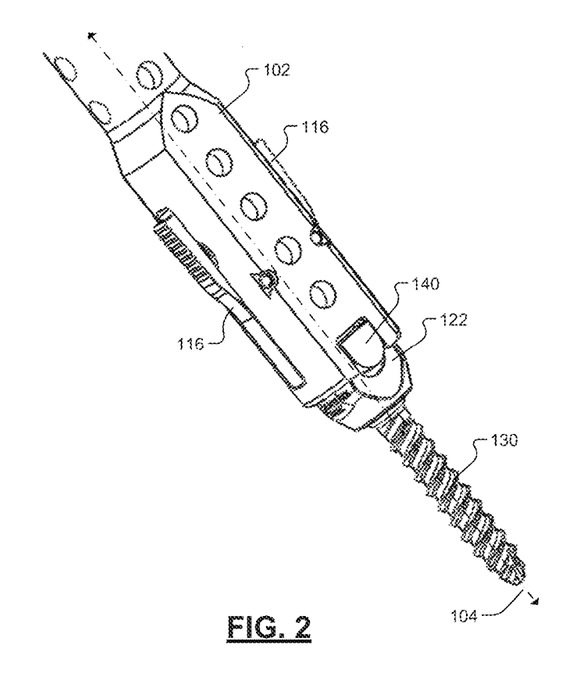
FIG. 2 is an enlarged view of the distal end of the instrument when the screw body is engaged with the distal end with the barrel body, according to the principles of the present disclosure.

As shown in FIGS. 1-2, an instrument 100 for provisionally locking a polyaxial screw body member to a screw generally comprises a barrel body 102 having a generally longitudinal axis 104, wherein the barrel body 102 includes a proximal end 108 and a distal end 110 generally along the longitudinal axis 104. An inner shaft 140 is coaxially disposed within the barrel body 102 and may be advanced distally along the longitudinal axis from a first position to a second position. The inner shaft 140 may be retracted proximally along the longitudinal axis to a first position. A handle 180 extends proximally from the proximal end 108 of the barrel body 102 for holding of the instrument 100 by an operator. A load link assembly 160 is operably coupled to the barrel body 102 and the inner shaft 140 near the proximal end 108 of the barrel body 102. The load link assembly 160 may be coupled to the barrel body 102 by any suitable method of attachment such as, for example, a fastener, an aperture, a nut or bolt connection, or the like. The load link assembly 160 may include two portions, 160a and 160b, coupled by one or more pins to each other and the handle 180. The portions 160a and 160b may rotate relative to one another to permit a change in the overall length of the load link assembly 160 when acted upon by the operator.

A lever 170 rotatably associates with the handle 180 and the lever 170 is operably coupled with the load link assembly 160. The lever 170 may extend from the load link assembly 160 via mechanical attachment by any suitable method of attachment, for example, a fastener, an aperture, a nut-bolt connection, a washer, or the like. Alternatively, the lever 170 and load link assembly 160 may be a unitary element that is mounted on the proximal end 108 of the barrel body 102.

In a first embodiment, actuation of the lever 170 causes the inner shaft 140 to longitudinally move towards the distal end to the second position, and release of the lever 170 causes the inner shaft 140 to longitudinally move towards the proximal end to the first position. In a second embodiment, actuation of the lever 170 causes the inner shaft 140 to longitudinally move towards the proximal end to the first position, and release of the lever 170 causes the inner shaft 140 to longitudinally move towards the distal end and the second position. In the first and second embodiments, returning the lever 170 to its original position causes the inner shaft 140 to return to its original position.

Figure 3A:
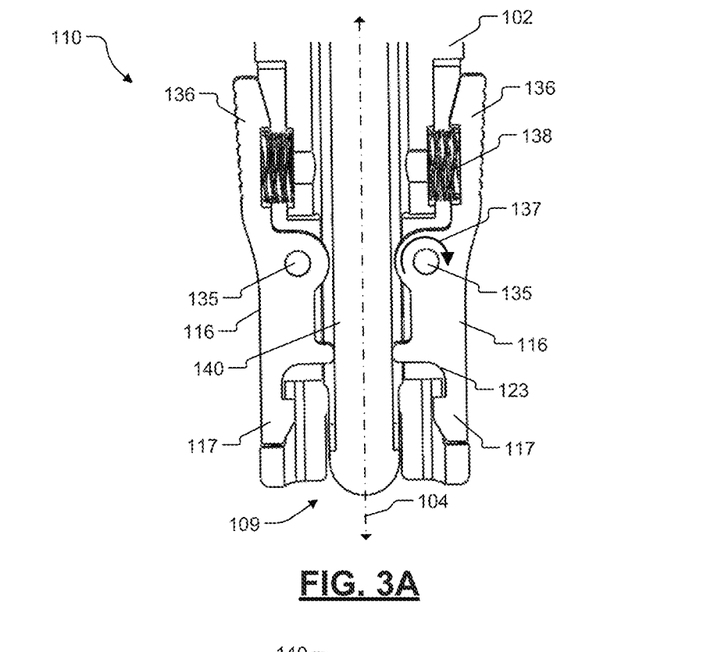
FIG. 3A is a cross-sectional view of the distal end of the instrument in a place extending through the longitudinal axis 104 and parallel to the sheet.
Figure 3B:
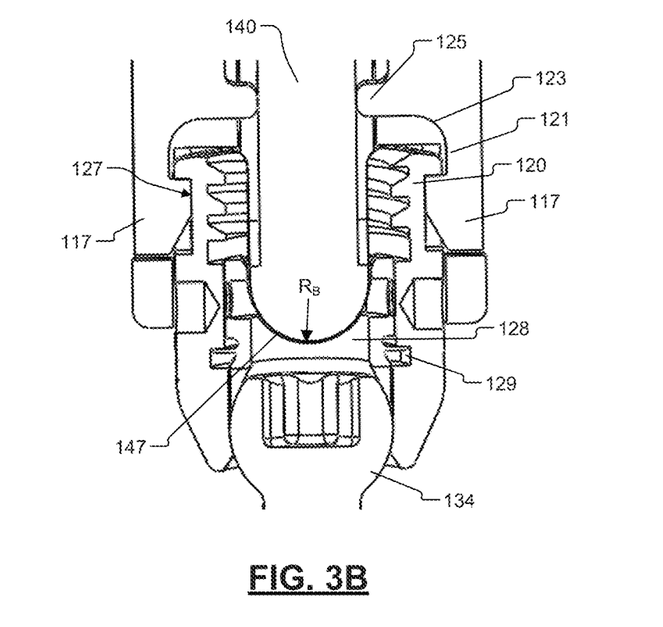
FIG. 3B is a cross-sectional view of the distal end of the instrument engaged with the screw body.

As shown in FIGS. 3A and 3B, the distal end 110 of the barrel body 102 includes an opening 109 to fit a screw body member 122 and a screw 130. The inner shaft 140 is operably coupled to the load link assembly 160, as shown in FIG. 1. The inner shaft 140 may be slidably disposed within the barrel body 102 and extends longitudinally through the proximal end of the barrel body 102 to the distal end 110 to the barrel body 102, such that the inner shaft 140 may be longitudinally displaced within the barrel body 102 by operation of the lever 170 and the load link assembly 160. The proximal end of the inner shaft 140 is operably coupled to the distal end of the load link assembly 160 to longitudinally displace the inner shaft 140 along the longitudinal axis 104 and through the opening 109. The longitudinal displacement of the inner shaft 140 forces a bushing 128 to be wedged between the screw head 134 and the body member 122. The lever 170 may extend downwardly from the load link assembly 160 and the barrel body 102 at an angled inclination, as shown in FIG. 1.

As shown in FIGS. 3A and 3B, the distal end 110 includes at least two tangs 116 that generally project and pivot along the longitudinal axis 104 and towards the distal end of the barrel body 102. The tangs 116 include at least one protrusion 117 that is positioned on the interior surface of the tang 116, such that the screw body member 122 may be secured in the distal end 110 of the barrel body 102, as shown in FIG. 3B. In one embodiment, the protrusion 117 radially extends inwardly from an interior surface of each of the tangs 116 proximate to a distal end of the tangs 116. The protrusion 117 defines a distal end of a groove 123 that may include a tapered proximal end 125. The protrusion 117 is adapted to engage a body pocket 120 (See also FIGS. 4A-4B) disposed on the screw body member 122. The distal end 121 of the groove 123 includes a generally right angled corner that is well suited for engaging the body pocket 120, locking the body pocket 120 into the distal end 110 of the barrel body 102, and applying a proximally directed force thereto. As such, the screw body member 122 may be locked in the distal end 110 of the barrel body 102. The protrusions 117 may include a generally angled or tapered surface on the distal end to abut the screw body member and permit the proximal portion of the screw body member 122 to slide over the generally angles surface and lock with the protrusion 117 and the body pocket 120.

In one embodiment, the protrusion 117 may include an exterior surface that may be the same general shape as the body pocket 120 to facilitate engagement of the body pocket 120 by the protrusion 117. For example, the protrusion 117 may have an exterior surface 127 that is generally rectangular like the body pocket 120 illustrated in FIGS. 4A-4B. However, the exterior surface of the protrusion may have any shape as desired to facilitate engagement of body pockets 120 having other shapes, including by way of example and not limitation, a circle, a rectangle, a pentagram, a hexagram, any regular polygon, any irregular polygon, and the like.

As shown in FIG. 3A, the tangs 116 include a proximal bar 136 on the proximal portion, which is operably coupled to at least one spring 138. The springs 138 may be operably coupled to the exterior portion of the barrel body 102. The springs 138 are pre-stressed such that the proximal bar 136 is displaced axially away from the longitudinal axis 104 and the tangs 116 are proximally displaced towards the longitudinal axis 104. The distal portion of the tangs 116 and the protrusions 117 are displaced away from the longitudinal axis 104 by rotation about the pins 135 as the barrel body 102 engages the screw body member 122. Therefore, the bias of the spring 138 and the proximal bar 136 of the tangs 116 axially displace or rotate the distal portion of the tangs 116 and the protrusion 117 axially away from the longitudinal axis 104, as the tangs 116 rotate about the pins 135. In alternative embodiments, the tangs 116 are integral with the distal end 110 of the barrel body 102. In other embodiment, the tangs 116 may be removable disposed/attachable in order to attach the tangs 116 having protrusions 117 that are able to engage screw body pockets 120 (as shown in FIGS. 4A-4B) having different shapes and/or sizes.

As shown in FIGS. 3A-3B, the tangs 116 axially displace the protrusions 117 towards the longitudinal axis 104 and engage the screw body pockets 120, as illustrated by the line 137. The proximal bar 136 and the spring 138 keep the protrusions 117 engaged with the screw body pockets 120, which allow the inner shaft 140 to engage a bushing 128 into the pedicle screw 130 to create a frictional lock. Releasing the lever 170 causes the inner shaft 140 to move proximally to disengage distal portion from the bushing 128 and the pedicle screw 130.

Figure 4A:
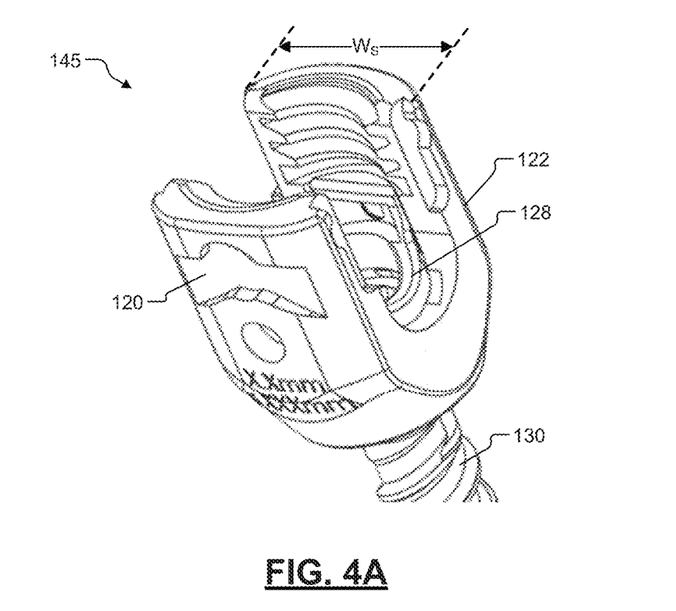
FIG. 4A is a generally top perspective view of the screw body member, the bushing, and the screw.
Figure 4B:
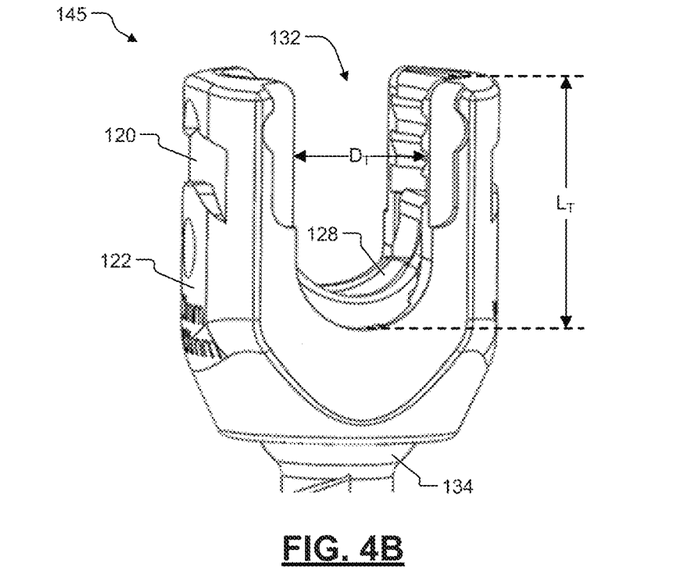
FIG. 4B is a generally side perspective view of the screw body member, the bushing, and the screw, according to the principles of the present disclosure.

Referring to FIGS. 4A-4B, for example, the tangs 116 may have a generally rectangular cross-sectional shape that is similarly shaped as at least a portion of the exterior surface of the screw body member 122 when the tangs 116 are engaged with the screw body member 122. Such a configuration of the exterior surface of the tangs 116 enhances engagement between the tangs 116 and the screw body member 122 and/or provides enhanced support against the screw body member 122 moving with respect to the tangs 116 when engaged by the tangs 116. The tangs 116 may include a cross-sectional shape looking along the longitudinal axis 104 that such that an interior surface of the distal portion of each tang 116 is complementary to a peripheral surface of the screw body member 122. Examples of screw body members 122 that may be useful in the current invention may be found in U.S. Patent Application Publication No. 2010/0318136, U.S. Patent Application Publication No. 2008/0243189, and U.S. Pat. No. 7,377,923, both of which are hereby incorporated by reference in their entirety herein. Alternatively, the instrument 100 may be used with any screw requiring a friction-fit bushing to be translated or displaced.

As shown in FIGS. 4A-4B, a polyaxial pedicle screw assembly 145 comprises the screw body member 122, a bushing 128, and a polyaxial pedicle screw 130. The screw body member 122 is generally cylindrical in configuration and adapted to receive a fixed head portion of the pedicle screw 130. The exterior surface of the screw body member 122 includes at least two body pockets 120, as to engage the protrusions 117. The screw body member 122 generally includes a width $W_S$. Traversing the exterior surface of the screw body member 122 is a generally tulip-shaped opening 132 that includes a length $L_T$ and a diameter $D_T$. The bushing 128 is adapted to coaxially fit within the screw body member 122 and partially extend between the screw body member 122 and a head portion 134 of the screw 130. In one embodiment, the bushing 128 has a concave proximal surface 147 that is adapted to mate with the distal engagement portion 141 of the inner shaft 140. In one embodiment, the concave proximal surface 147 includes a radius of curvature $R_B$. The bushing 128 has a slotted lower skirt portion (not shown) with tapered distal surfaces adapted to provide a press fitment or wedge about the head portion 134 of the pedicle screw 130. When the bushing 128 is compressed, it is wedged between the spherical head of the screw and the walls of the screw body member 122 for a frictional fit to resist movement of the body member 122 relative to the head portion 134. Once the bushing 128 has been locked in place by the inner shaft 140, the polyaxial motion of the screw head 134, even when active pressure of the inner shaft 140 is removed from the bushing 128, is restricted.

The pedicle screw 130 may include a substantially spherical or elliptical head portion 134 defining a slot therein used to drive a threaded shaft portion of the screw 130 into a vertebra or other bone. Examples of bushings 128 and polyaxial pedicle screws 130 that may be useful in the current invention may be found in U.S. Patent Application Publication No. 2010/0318136, U.S. Patent Application Publication No. 2008/0243189, and U.S. Pat. No. 7,377,923, all incorporated by reference herein. Typically, the set screw is used to compress rod into the bushing to lock the body member and head portion of the screw in a single action.

In operation, the instrument 100 of the present disclosure allows an operator to provisionally tighten the screw head portion 134 without inserting a rod and set screw into the pedicle screw. If the provisionally tightened screw needs to be adjusted, the screw may be loosened without the rod and the bushing being re-inserted and then removed again. An operator may apply compression and distraction forces to the screw body member 233 and achieve direct compression and distraction. Once the desired compression or distraction is achieved, the operator can then insert the rod and set screws and final tightening torques if necessary.

Figure 5A:
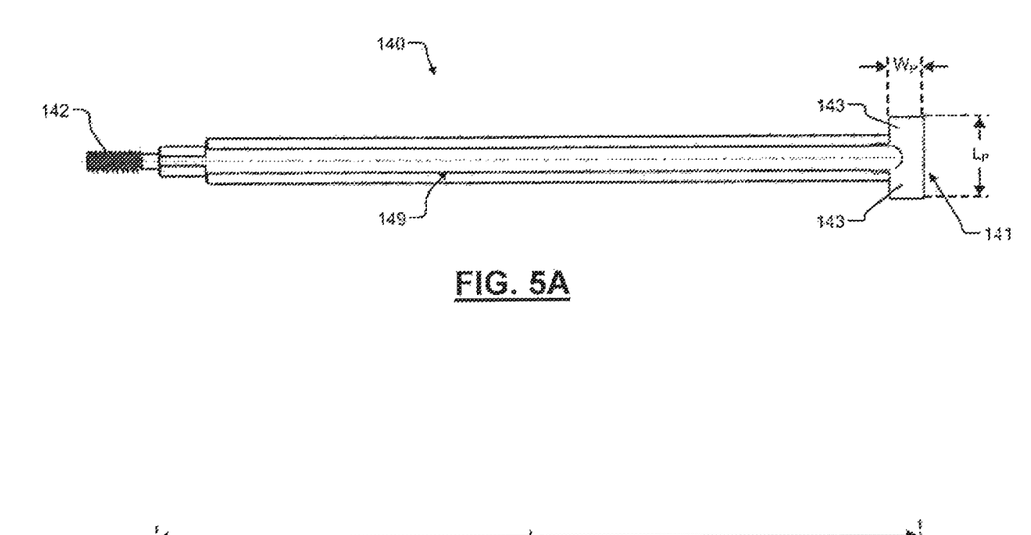
FIG. 5A is side view of an inner shaft, according to the principles of the present disclosure.
Figure 5B:
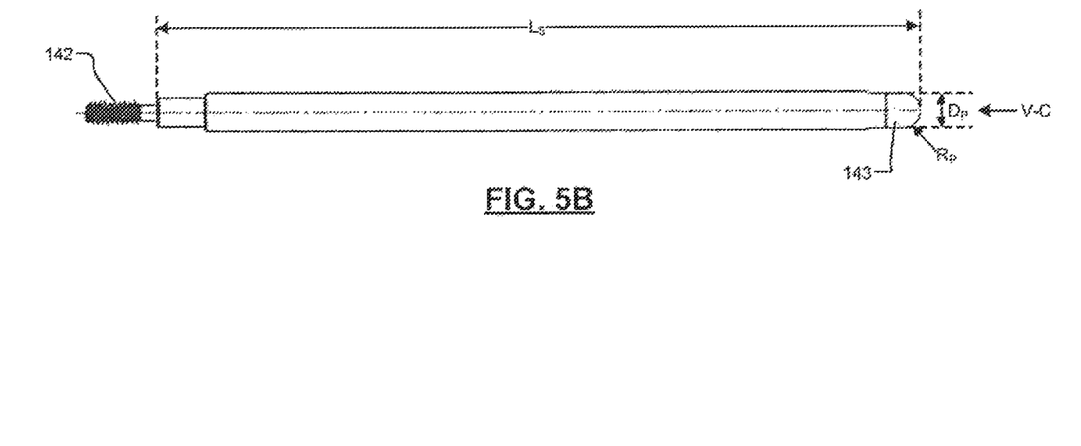
FIG. 5B is side view of the inner shaft, according to the principles of the present disclosure.

As shown in FIG. 5A-5B, the inner shaft 140 includes a distal engagement portion 141 on the distal end and the proximal end of the inner shaft 140 includes a generally threaded portion 142 to be operably coupled to the load link assembly 160. The distal engagement portion 141 generally includes at least two projections 143 extending from the longitudinal axis of the inner shaft 140 that include a length $L_P$ and a width $W_P$. In one embodiment, the Width $W_P$ of the distal engagement portion 141 is about equal to or greater than the length $L_T$ of the tulip-shaped opening 132 of the screw body member 122, such that the longitudinal movement of the inner shaft 140 towards the distal end is able to engage the bushing 128. The distal engagement portion 141 includes a radius of curvature $R_P$, which substantially equals the radius of curvature $R_B$ of the concave surface 147 of the bushing 128, as to allow a flush engagement of the distal engagement portion 141 with the concave surface 147 of the bushing 128. The distal engagement portion 141 includes a diameter $D_P$ that is less than or equal to the diameter $D_T$ of the tulip shaped opening 132 of the body screw member 122, which allows the distal engagement portion 141 to be longitudinally displaced within the tulip-shaped opening 132.

Figures 5C, 6:
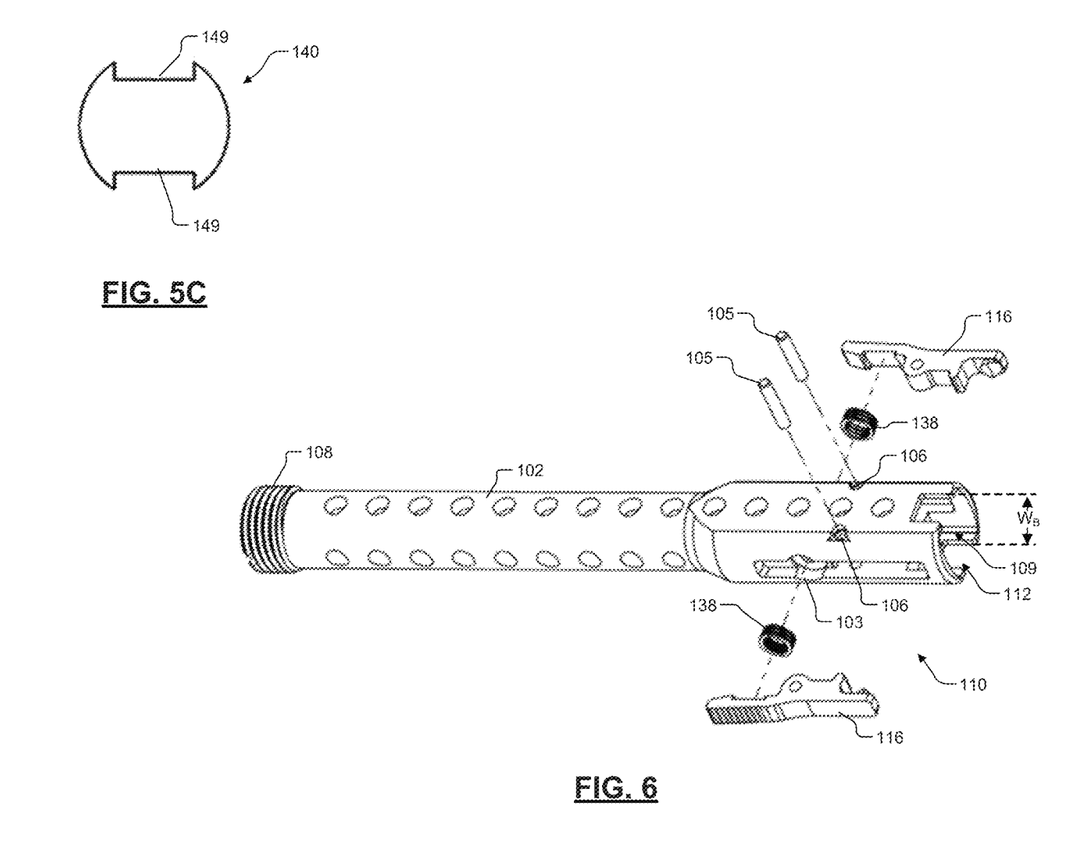
FIG. 5C is side view of the inner shaft taken from the perspective of arrow V-C in FIG. 5B, according to the principles of the present disclosure.
FIG. 6 is a perspective exploded view of a barrel body of the instrument.

Alternatively, the inner shaft 140 may include generally stepped profile whereby the distal portion of the inner shaft 140 includes a smaller diameter than the middle portion, and the middle portion includes a smaller diameter than the proximal portion. Although the inner shaft 140 is generally shown to have H-shaped cross-sections, alternative configurations for the cross-section of the inner shaft 140 may be used, for example, circular, square, elliptical, polygonal cross-sections, and the like configurations. As shown in FIGS. 5A and 5C, the inner shaft 140 may optionally include a longitudinal slide or cutout 149, as to permit the inner shaft 140 to longitudinally slide along the inner lumen of the barrel body 102. The inner lumen of the barrel body 102 may have a reciprocal or corresponding inner longitudinal slide or cutout to operably couple the inner shaft 140 with the barrel body 102 for longitudinal displacement.

As shown in FIG. 6, the barrel body 102 is operably coupled with the tangs 116 on the distal end 110 by way of at least two pins 105 that are fixed within holes 106 on the distal end 110. The springs 138 operably coupled with the tangs 116 are seated within a stepped portion 103 on the distal end 110 of the barrel body 102. The distal end 110 further includes at least two cutouts 112 that seat the at least two protrusions 143 of the distal engagement portion 141 of the inner shaft 140. In one embodiment, the proximal end 108 of the barrel body 102 includes a threaded portion for fixedly associating the barrel body 102 to the handle 180. In one embodiment, the distal end 110 of the barrel body 102 includes an opening 109 with a width $W_B$ that is greater than or equal to the width $W_T$ of the screw body member 122, such that the screw body member 122 coaxially fits within the opening 109 on the distal end 110. The barrel body 102 is generally cylindrical in shape; however, it may assume alternative cross-sectional shapes such as circular, elliptical, square, rectangular, polygonal, and the like.

Figure 7:
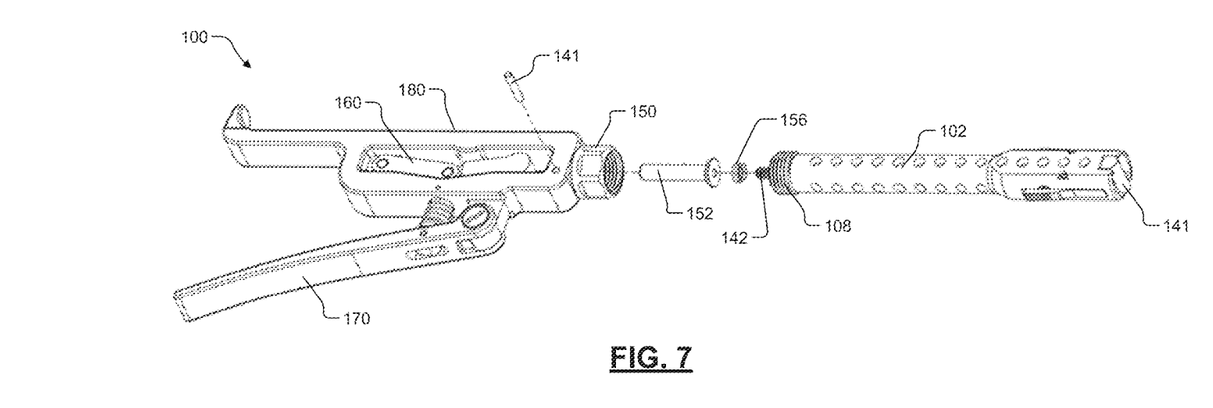
FIG. 7 is a perspective view of the inner shaft coaxially disposed within the barrel body and being coupled to the handle and load link assembly.
Figure 8:
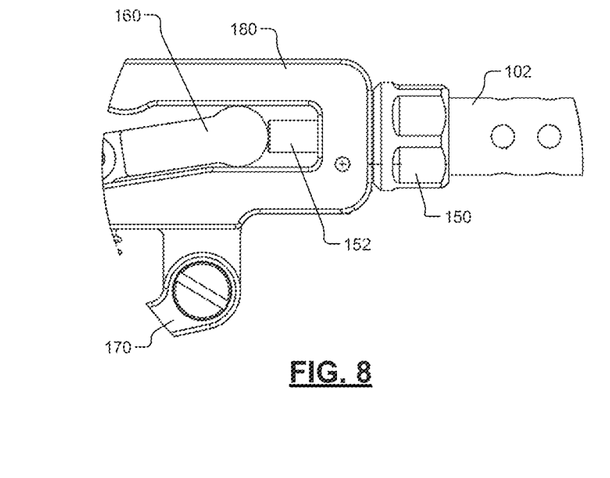
FIG. 8 is a side view of the barrel body operably coupled to the handle.
Figure 9:
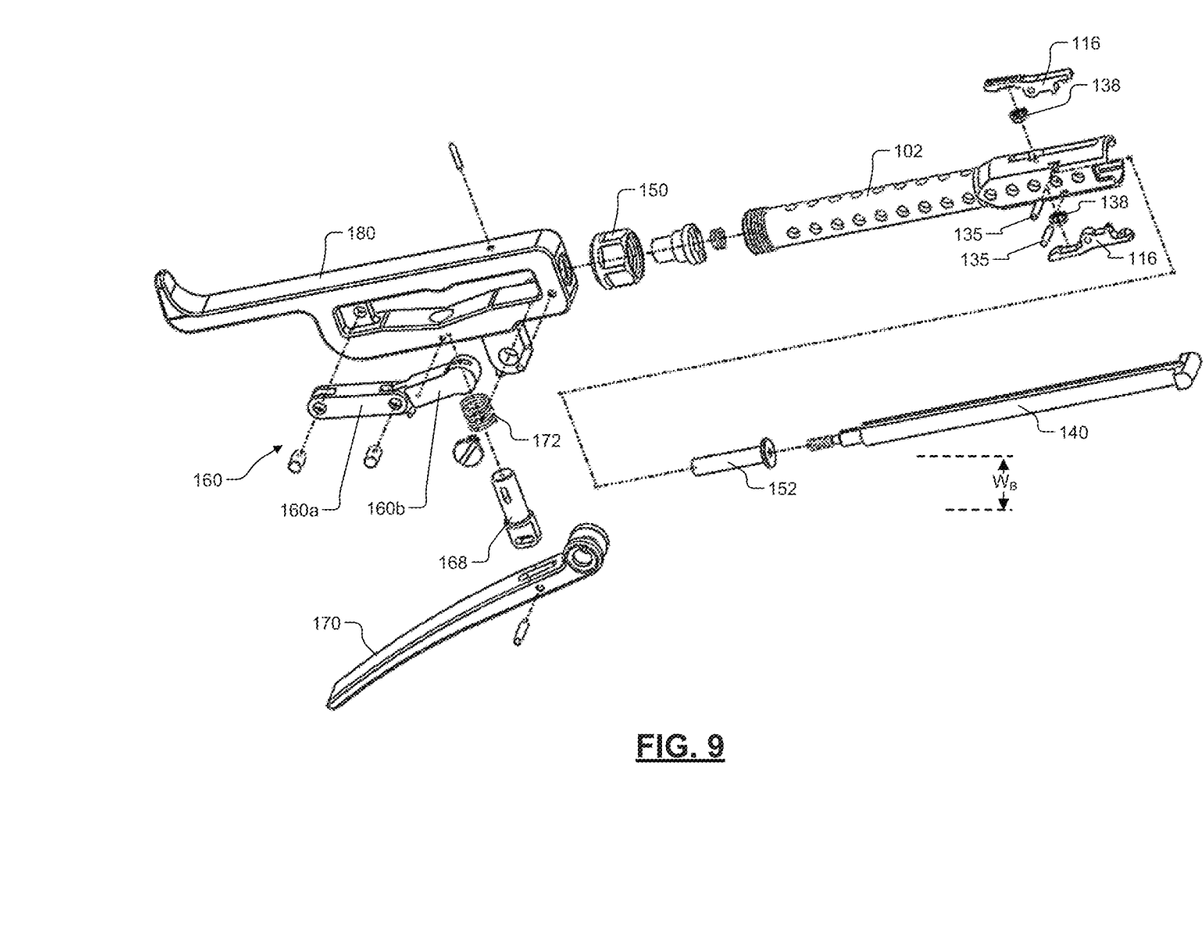
FIG. 9 is a perspective exploded view of the instrument, according to the principles of the present disclosure.

As shown in FIG. 7, the inner shaft 140 is coaxially coupled within the barrel body 102, whereby the proximal end 142 of the inner shaft 140 protrudes from the proximal end 108 of the barrel body 102. In one embodiment, the proximal end 142 of the inner shaft 140 is operably associated with a retention cap 152 and a spring 156, while the proximal end 108 of the barrel body 102 is fixedly associated with a retention collar 150, as shown in FIGS. 7 and 9. As shown in FIG. 8, the retention cap 152 is coaxially disposed through the retention collar 150 and the distal end of the handle 180. The retention collar 150 is fixedly associated with the distal end of the handle 180. The retention cap 152 is operably associated with the load link assembly 160, such that the longitudinal displacement of the load link assembly 160 longitudinally displaces the retention cap 152 along with the inner shaft 140.

Operation of the lever 170 longitudinally displaces the load link assembly 160 by way of a transfer link 168 and a spring 172, as shown in the exploded FIG. 9. The spring 172 biases the lever 170 away from the handle 180, and when the lever 170 is moved towards the handle 180 by an operator, the transfer link 168 longitudinally displaces the load link assembly 160 to longitudinally displace the inner shaft 140. For example, the transfer link 168 may act on a pivot point between portion 160a and 160b. In some embodiments, the lever 170 and the load link assembly 160 may be associated with a locking and/or moving mechanism at the proximal end 108, for example, a ratcheting mechanism, for incrementally locking and/or distally moving the inner shaft 140 towards the distal end 110 and subsequently releasing the inner shaft 140 to be moved towards the proximal end 108 of the barrel body 102. Alternative spring locked or spring hinged mechanisms may be coupled to the load link assembly 160 and the lever 170 to move the inner shaft 140 distally and proximally within the barrel body 102 in incremental or stepped positions.

A screw head locker for spinal immobilization systems is presented. The screw head locker includes a screw body member that is provisionally tightened before placing a rod or set screw into the screw body member. Such provisional tightening allows the screw body member to be frictionally locked at a specific angle relative to a polyaxial pedicle screw prior to rod or set screw introduction.

As can be understood by one skilled in the art, the screw head locker 100 and/or any of its components may have any size, shape, length, thickness, height, weight, or any other parameters. Such parameters may be selected by the surgeon (or other qualified professional) for performance of specific procedures. Further, the screw head locker 100 and/or any of its components may be manufactured from metal, plastic, synthetic material, or other suitable materials, or any combination thereof. In one embodiment, the screw head locker 100 is composed of titanium, nitinol, or stainless steel, or any medical grade polymer, such as Polyether ether keton (PEEK).

In some embodiments, various lengths and configurations may also include various features to accommodate different applications for the screw head locker. The screw head locker can be constructed of various materials to aid in radio translucency, strength, flexibility, and integration with anatomy, etc.

It will be appreciated by those skilled in the art that changes could be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the screw head locker described herein and to teach the best mode of carrying out the same.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. A screw head locker assembly for tightening a screw body member to a head of a polyaxial bone screw, the screw head locker assembly comprising:
    a bushing configured to be seated between the head and the screw body member of the polyaxial bone screw, the bushing having a concave surface having a radius of curvature $R_b$;
    a barrel body having a proximal end and a distal end, the distal end having a pair of tangs for releasably engaging a screw body pocket on the screw body member, and a pair of cut outs opposite of each other and open to the distal end of the barrel body;

an inner shaft coaxially disposed between the pair of tangs, wherein the inner shaft includes a distal engagement portion, the distal engagement portion having a pair of opposing protrusions extending from a longitudinal axis of the inner shaft so as to be orthogonal to the longitudinal axis of the inner shaft and each protrusion configured to be seated within a respective cut out of the pair of cut outs, the pair of opposing protrusions cooperatively having a length $L_P$, the pair of opposing protrusions having a radius of curvature $R_p$ which substantially equals the radius of curvature $R_b$ of the concave surface of the bushing of the screw body member, the pair of cutouts spaced apart from each other a length $W_b$, wherein the length $L_p$ is greater than $W_b$; and a lever operably coupled to the inner shaft, wherein the lever distally displaces the pair of opposing protrusion to engage with the bushing to lock the polyaxial motion of a screw displaced beneath the bushing.

2. The screw head locker as described in claim 1, wherein the lever is operably coupled to a load link assembly to distally displace the inner shaft into the screw body member to contact the bushing.

3. The screw head locker as described in claim 2, wherein the load link assembly includes first and second portions pivotally coupled together and coupled to the lever by a transfer link.

4. A screw head locker assembly for provisionally tightening a screw body member to a head of a polyaxial bone screw the screw head locker assembly comprising:

a bushing configured to be seated between the head and the screw body member of the polyaxial bone screw, the bushing having a concave surface having a radius of curvature $R_b$;

a barrel body having a proximal end and a distal end, the distal end having a pair of tangs for releasably engaging a pair of screw body pockets on the screw body member, and a pair of cut outs opposite of each other and open to the distal end of the barrel body;

an inner shaft disposed within the barrel body, the inner shaft having a distal engagement portion with a pair of opposing protrusions extending from a longitudinal axis of the inner shaft, the pair of opposing protrusions cooperatively having a length $L_P$ and a radius of curvature $R_p$ which substantially equals the radius of curvature $R_b$ of the concave surface of the bushing of the screw body member, the pair of cutouts spaced apart from each other a length $W_b$, wherein the length $L_p$ is greater than $W_b$;

a load link assembly operably coupling the inner shaft to the body, and a lever extending from the load link assembly, the lever being movable to actuate the load link assembly, wherein the actuation of the load link assembly displaces the pair of opposing protrusions to engage the bushing disposed between the screw body member and the head of the polyaxial bone screw.

5. The screw head locker as described in claim 4, wherein the inner shaft is longitudinally disposed between the pair of tangs.

6. The screw head locker as described in claim 4, wherein displacement of the lever after load link assembly actuation longitudinally displaces the distal engagement portion of the inner shaft proximally from the bushing.

7. A screw head locker assembly for provisionally tightening a screw body member to a head of a polyaxial bone screw, the screw head locker assembly comprising:

a bushing configured to be seated between the head and the screw body member of the polyaxial bone screw, the bushing having a concave surface having a radius of curvature $R_b$;

a barrel body having a proximal end and a distal end, the distal end having a pair of rotatable tangs configured to engage the screw body member, and a pair of cut outs opposite of each other and open to the distal end of the barrel body;

an inner shaft including a proximal end and a distal end configured to engage a bushing within the screw body member, the bushing having a concave surface having a curvature of radius $R_b$, the inner shaft having a distal engagement portion with a pair of opposing protrusions extending from a longitudinal axis of the inner shaft and configured to be seated within a respective cut out of the pair of cut outs, the pair of protrusions cooperatively having a length $L_P$, the two opposing protrusions having a radius of curvature $R_p$ which substantially equals the radius of curvature $R_b$ of the concave surface of the bushing of the screw body member, wherein the pair of cutouts are spaced apart from each other a length $W_b$, wherein the length $L_p$ is greater than $W_b$;

a handle and a lever coupled to the proximal end of the barrel body, the lever pivotally coupled to one of the handle and the barrel body; and a load link assembly operably coupled to the inner shaft and the lever, wherein actuation of the lever towards the handle causes the load link assembly to longitudinally displace the pair of opposing protrusions toward the distal end to contact the bushing and advance the bushing into a frictional fit between the screw body member and the head of the polyaxial bone screw.

8. The screw head locker assembly as described in claim 7, wherein the pair of tangs are adapted to releasably engage a pair of screw body pockets.

9. The screw head locker assembly as described in claim 7, wherein the inner shaft is coaxially disposed between the pair of tangs.

10. The screw head locker assembly according to claim 7, wherein the lever is movable to actuate the load link assembly.

11. The screw head locker assembly according to claim 7, wherein displacement of the lever after load link assembly actuation longitudinally displaces the distal engagement portion of the inner shaft towards the proximal end of the barrel body.

12. The screw head locker assembly of claim 7, further comprising a bias spring to bias the lever away from the handle to return the load link assembly to a rest position, wherein the inner shaft advances away from the distal end and the pair of protrusions of the distal engagement portion are seated within the pair of cutouts of the distal end of the barrel body.

13. The screw head locker assembly of claim 7, wherein the load link assembly comprises first and second portions pivotally coupled together such that actuation of the lever causes the at least one of the first and second portions to advance towards a proximal end of the inner shaft.

14. The screw head locker assembly of claim 7, wherein the pair of tangs are biased towards engagement with the screw body member by a pair of bias members within the distal end of the barrel body.

* * * * *